United States Patent
Root et al.

(10) Patent No.: US 10,729,454 B2
(45) Date of Patent: Aug. 4, 2020

(54) GUIDEWIRE CAPTURE

(71) Applicant: Teleflex Life Sciences Limited, Valletta (MT)

(72) Inventors: Howard C. Root, Excelsior, MN (US); Dean Peterson, Rogers, MN (US); Joshua Brenizer, Maple Grove, MN (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

(21) Appl. No.: 14/709,531

(22) Filed: May 12, 2015

(65) Prior Publication Data
US 2016/0066933 A1    Mar. 10, 2016

Related U.S. Application Data

(60) Provisional application No. 62/048,734, filed on Sep. 10, 2014.

(51) Int. Cl.
| | |
|---|---|
| *A61B 17/221* | (2006.01) |
| *A61B 17/50* | (2006.01) |
| *A61B 17/22* | (2006.01) |

(52) U.S. Cl.
CPC ............ *A61B 17/221* (2013.01); *A61B 17/50* (2013.01); *A61B 2017/22001* (2013.01);
(Continued)

(58) Field of Classification Search
CPC .................. A61B 17/221; A61B 17/50; A61B 2017/22001; A61B 2017/22035;
(Continued)

(56) References Cited

U.S. PATENT DOCUMENTS

| | | | |
|---|---|---|---|
| 4,762,130 | A | 8/1988 | Fogarty et al. |
| 4,909,252 | A | 3/1990 | Goldberger |
| (Continued) | | | |

FOREIGN PATENT DOCUMENTS

| | | |
|---|---|---|
| EP | 1815823 B1 | 12/2008 |
| EP | 1587447 B1 | 9/2012 |
| (Continued) | | |

OTHER PUBLICATIONS

Spectranetics. "Quick-Cross Capture Guidewire Retriever" [brochure]. Colorado Springs, CO: Spectranetics Corporation, 2013 [retrieved on Sep. 3, 2014]. Retrieved from the Internet: <http://www.spectranetics.com/wp-content/uploads/2013/01/D019438-01-QuickCrossCapture.pdf>.
(Continued)

*Primary Examiner* — Todd J Scherbel
*Assistant Examiner* — Mikail A Mannan
(74) *Attorney, Agent, or Firm* — Gregory W. Smock; Robert B. Madden

(57) ABSTRACT

Assemblies and methods for capturing a guidewire advanced through a blood vessel in a retrograde direction are disclosed. An assembly can include a constraining catheter and a capture catheter. The constraining catheter can include a first longitudinal member and a tubular member; the tubular member can be eccentrically coupled with a distal end portion of the first longitudinal member. The capture catheter can include a second longitudinal member and a funnel member; the funnel member can be eccentrically coupled with a distal end portion of the second longitudinal member. The funnel member can be moved between a collapsed configuration and an expanded configuration through relative movement between the first and second longitudinal members. In the collapsed configuration, at least a portion of the funnel member is disposed within a lumen of the tubular (Continued)

US 10,729,454 B2

Page 2 member. In the expanded configuration, the portion of the funnel member projects from an end of the tubular member.

15 Claims, 9 Drawing Sheets

(52) U.S. Cl.
CPC .............. *A61B 2017/2215* (2013.01); *A61B 2017/22035* (2013.01); *A61B 2017/22038* (2013.01); *A61B 2017/22044* (2013.01); *A61B 2017/22069* (2013.01); *A61B 2017/22094* (2013.01)

(58) Field of Classification Search
CPC ........... A61B 2017/22038; A61B 2017/22044; A61B 2017/22069; A61B 2017/22094; A61B 2017/2215; A61M 25/09041
See application file for complete search history.

(56) References Cited

U.S. PATENT DOCUMENTS

| | | |
|---|---|---|
| 4,944,745 A | 7/1990 | Sogard et al. |
| 5,047,045 A | 9/1991 | Arney et al. |
| 5,087,247 A | 2/1992 | Horn et al. |
| 5,181,911 A | 1/1993 | Shturman |
| 5,195,969 A | 3/1993 | Wang et al. |
| 5,226,888 A | 7/1993 | Arney |
| 5,226,889 A | 7/1993 | Sheiban |
| 5,252,159 A | 10/1993 | Arney |
| 5,257,974 A | 11/1993 | Cox |
| 5,290,247 A * | 3/1994 | Crittenden ........ A61M 25/0169 604/171 |
| 5,290,310 A | 3/1994 | Makower et al. |
| 5,368,566 A | 11/1994 | Crocker |
| 5,370,617 A * | 12/1994 | Sahota ................ A61M 25/104 604/102.02 |
| 5,370,691 A | 12/1994 | Samson |
| 5,421,826 A | 6/1995 | Crocker et al. |
| 5,439,445 A | 8/1995 | Kontos |
| 5,470,314 A | 11/1995 | Walinsky |
| 5,505,702 A | 4/1996 | Arney |
| 5,536,250 A | 7/1996 | Klein et al. |
| 5,545,135 A | 8/1996 | Iacob et al. |
| 5,549,552 A | 8/1996 | Peters et al. |
| 5,554,119 A | 9/1996 | Harrison et al. |
| 5,556,382 A | 9/1996 | Adams |
| 5,558,642 A | 9/1996 | Schweich et al. |
| 5,569,184 A | 10/1996 | Crocker et al. |
| 5,613,948 A | 3/1997 | Avellanet |
| 5,643,171 A | 7/1997 | Bradshaw et al. |
| 5,649,978 A | 7/1997 | Samson |
| 5,690,642 A | 11/1997 | Osborne et al. |
| 5,716,340 A | 2/1998 | Schweich et al. |
| 5,720,723 A | 2/1998 | Adams |
| 5,738,667 A | 4/1998 | Solar |
| 5,800,450 A | 9/1998 | Lary et al. |
| 5,855,546 A | 1/1999 | Hastings et al. |
| 5,879,369 A | 3/1999 | Ishida |
| 5,882,290 A | 3/1999 | Kume |
| 5,891,154 A | 4/1999 | Loeffler |
| 5,935,114 A | 8/1999 | Jang et al. |
| 5,961,490 A | 10/1999 | Adams |
| 6,083,215 A | 7/2000 | Milavetz |
| 6,110,097 A | 8/2000 | Hastings et al. |
| 6,187,014 B1 | 2/2001 | Goodin et al. |
| 6,190,355 B1 | 2/2001 | Hastings |
| 6,245,040 B1 | 6/2001 | Inderbitzen et al. |
| 6,361,529 B1 | 3/2002 | Goodin et al. |
| 6,371,971 B1 * | 4/2002 | Tsugita ..................... A61F 2/01 606/200 |
| 6,379,319 B1 | 4/2002 | Garibotto et al. |
| 6,387,119 B2 | 5/2002 | Wolf et al. |
| 6,503,224 B1 | 1/2003 | Forman et al. |
| 6,506,180 B1 | 1/2003 | Lary |
| 6,673,090 B2 | 1/2004 | Root et al. |
| 6,945,957 B2 | 9/2005 | Freyman |
| 6,945,977 B2 | 9/2005 | Demarais et al. |
| 7,147,655 B2 | 12/2006 | Chermoni |
| 7,232,452 B2 | 6/2007 | Adams et al. |
| 7,517,352 B2 | 4/2009 | Evans et al. |
| 7,563,247 B2 | 7/2009 | Maguire et al. |
| 7,918,859 B2 | 4/2011 | Katoh et al. |
| 7,938,819 B2 | 5/2011 | Kugler et al. |
| 8,048,032 B2 | 11/2011 | Root et al. |
| 8,167,902 B2 | 5/2012 | Quinn et al. |
| 8,172,772 B2 | 5/2012 | Zwolinski et al. |
| 8,241,311 B2 | 8/2012 | Ward et al. |
| 8,323,261 B2 | 12/2012 | Kugler et al. |
| 8,430,845 B2 | 4/2013 | Wahr et al. |
| 8,469,925 B2 | 6/2013 | Rowe et al. |
| 8,486,014 B2 | 7/2013 | Kelly et al. |
| 8,636,712 B2 | 1/2014 | Kugler et al. |
| 8,696,699 B2 | 4/2014 | Chomas et al. |
| 8,961,494 B2 | 2/2015 | Kugler et al. |
| 8,974,482 B2 | 3/2015 | Shriver |
| 9,301,777 B2 | 4/2016 | Silvestro |
| 9,308,356 B2 | 4/2016 | Silvestro |
| 9,364,642 B2 | 6/2016 | Sina |
| 9,446,222 B2 | 9/2016 | Silvestro |
| 9,878,128 B2 | 1/2018 | Kugler et al. |
| 9,968,763 B2 | 5/2018 | Root et al. |
| 10,159,821 B2 | 12/2018 | Root et al. |
| 10,172,632 B2 | 1/2019 | Morero et al. |
| 10,245,050 B2 | 4/2019 | Kugler |
| 2002/0169458 A1 | 11/2002 | Connors |
| 2003/0032920 A1 | 2/2003 | Wantink |
| 2003/0040704 A1 | 2/2003 | Dorros et al. |
| 2003/0050600 A1 | 3/2003 | Ressemann et al. |
| 2003/0093090 A1 | 5/2003 | McGuckin et al. |
| 2003/0120195 A1 | 6/2003 | Milo et al. |
| 2003/0233068 A1 | 12/2003 | Jayaraman |
| 2004/0049152 A1 | 3/2004 | Nayak |
| 2004/0093008 A1 | 5/2004 | Zamore |
| 2004/0142704 A1 | 7/2004 | Scholz |
| 2004/0230178 A1 | 11/2004 | Wu |
| 2005/0075662 A1 | 4/2005 | Pedersen et al. |
| 2005/0154447 A1 | 7/2005 | Goshgarian |
| 2005/0177130 A1 * | 8/2005 | Konstantino ........ A61M 25/10 606/194 |
| 2005/0209559 A1 | 9/2005 | Thornton et al. |
| 2005/0209678 A1 * | 9/2005 | Henkes ............ A61B 17/12118 623/1.12 |
| 2005/0267442 A1 | 12/2005 | Oepen |
| 2006/0049152 A1 | 3/2006 | Matus |
| 2006/0074474 A1 | 4/2006 | Theron |
| 2006/0142704 A1 | 6/2006 | Lentz |
| 2006/0200191 A1 | 9/2006 | Zadno-Azizi |
| 2006/0210605 A1 | 9/2006 | Chang et al. |
| 2006/0224176 A1 * | 10/2006 | Fung ..................... A61F 2/013 606/200 |
| 2007/0093779 A1 | 4/2007 | Kugler et al. |
| 2007/0093781 A1 | 4/2007 | Kugler et al. |
| 2007/0208368 A1 | 9/2007 | Katoh et al. |
| 2008/0015541 A1 * | 1/2008 | Rosenbluth ...... A61B 17/22032 604/509 |
| 2008/0058836 A1 | 3/2008 | Moll et al. |
| 2008/0082051 A1 | 4/2008 | Miller et al. |
| 2008/0114390 A1 * | 5/2008 | Guinan ........... A61M 25/09041 606/194 |
| 2008/0200896 A1 * | 8/2008 | Shmulewitz ..... A61B 17/22032 604/500 |
| 2008/0306499 A1 | 12/2008 | Katoh et al. |
| 2008/0312681 A1 * | 12/2008 | Ansel ............... A61B 17/22031 606/200 |
| 2009/0105641 A1 | 4/2009 | Nissl |
| 2009/0124899 A1 | 5/2009 | Jacobs et al. |
| 2009/0177259 A1 | 7/2009 | Ning et al. |
| 2009/0254114 A1 | 10/2009 | Hirszowicz et al. |
| 2009/0264826 A1 | 10/2009 | Thompson |
| 2011/0009818 A1 | 1/2011 | Goff |
| 2011/0264039 A1 | 10/2011 | Thielen et al. |

(56) References Cited

U.S. PATENT DOCUMENTS

| | | | |
|---|---|---|---|
| 2012/0136382 A1 | 5/2012 | Kugler et al. | |
| 2012/0245520 A1 | 9/2012 | Kelly et al. | |
| 2012/0259214 A1 | 10/2012 | Solar et al. | |
| 2012/0289983 A1 | 11/2012 | Ogata et al. | |
| 2013/0072957 A1 | 3/2013 | Anderson | |
| 2013/0103070 A1 | 4/2013 | Kugler et al. | |
| 2013/0178887 A1 | 7/2013 | Rosenschein et al. | |
| 2013/0204278 A1 | 8/2013 | Cully et al. | |
| 2013/0261729 A1 | 10/2013 | Gillick et al. | |
| 2013/0274674 A1 | 10/2013 | Fischell et al. | |
| 2013/0317485 A1 | 11/2013 | Lupton | |
| 2014/0018773 A1 | 1/2014 | Wang et al. | |
| 2014/0025086 A1* | 1/2014 | Rottenberg | A61B 17/22 606/127 |
| 2014/0031918 A1* | 1/2014 | Newell | A61F 2/82 623/1.12 |
| 2014/0171958 A1 | 6/2014 | Baig | |
| 2014/0277068 A1 | 9/2014 | Kugler et al. | |
| 2015/0032148 A1 | 1/2015 | Golan | |
| 2015/0051633 A1 | 2/2015 | Sina | |
| 2015/0196360 A1 | 7/2015 | Grantham et al. | |
| 2015/0209065 A1 | 7/2015 | Dahm et al. | |
| 2016/0008584 A1 | 1/2016 | Root et al. | |
| 2016/0045219 A1 | 2/2016 | Guala et al. | |
| 2016/0066932 A1 | 3/2016 | Root et al. | |
| 2016/0074627 A1 | 3/2016 | Cottone | |
| 2016/0250448 A1 | 9/2016 | Copeta et al. | |
| 2017/0050003 A1 | 2/2017 | Root et al. | |
| 2017/0079671 A1 | 3/2017 | Morero et al. | |
| 2017/0143355 A1 | 5/2017 | Nicholson et al. | |
| 2018/0092650 A1 | 4/2018 | Kugler | |
| 2018/0333162 A1 | 11/2018 | Saab | |
| 2019/0083760 A1 | 3/2019 | Root et al. | |

FOREIGN PATENT DOCUMENTS

| | | |
|---|---|---|
| FR | 3018195 A1 | 9/2015 |
| JP | H09164191 A | 6/1997 |
| JP | 2002503986 A | 2/2002 |
| JP | 2005230579 A | 9/2005 |
| JP | 2011505918 A | 3/2011 |
| JP | 6097447 | 2/2017 |
| JP | 6326517 B2 | 4/2018 |
| WO | 1993007929 A1 | 4/1993 |
| WO | 1994026206 A1 | 11/1994 |
| WO | 1997032626 A2 | 9/1997 |
| WO | 1998055179 A1 | 12/1998 |
| WO | 2000020064 A1 | 4/2000 |
| WO | 2000023139 A1 | 4/2000 |
| WO | 2001097697 A1 | 12/2001 |
| WO | 2005027995 A2 | 3/2005 |
| WO | 2004039290 | 9/2005 |
| WO | 2009122300 A2 | 10/2009 |
| WO | 2011129915 A2 | 10/2011 |
| WO | 2012037507 A1 | 3/2012 |
| WO | 2012141749 A1 | 10/2012 |
| WO | 2014037836 A1 | 3/2014 |
| WO | 2014055547 A1 | 4/2014 |
| WO | 2015105930 A1 | 7/2015 |
| WO | 2016025324 A1 | 2/2016 |
| WO | 2016040579 A1 | 3/2016 |

OTHER PUBLICATIONS

Advisory Action dated Oct. 27, 2016, in connection with U.S. Appl. No. 14/850,095.
Amendment After Final, filed Oct. 14, 2016, in connection with U.S. Appl. No. 14/850,095.
European Office Action dated Mar. 29, 2017, in related application EP 15770712.6 filed Sep. 10, 2015.
Final Rejection dated May 3, 2017, in U.S. Appl. No. 14/850,095.
Final Rejection dated Oct. 6, 2016, in connection with U.S. Appl. No. 14/850,095.
International Search Report dated Nov. 24, 2015, from corresponding PCT application PCT/US2015/049356 filed Sep. 10, 2015.
Non-final office action dated Mar. 22, 2017, in U.S. Appl. No. 14/850,095, filed Sep. 10, 2015.
Office Action dated Sep. 29, 2016, in corresponding Japanese Patent Application 2016-515958 filed Sep. 10, 2015 (PCT filing date).
Office Action dated Sep. 9, 2016, in connection with U.S. Appl. No. 14/850,095.
Request for Continued Examination filed Nov. 4, 2016, in connection with U.S. Appl. No. 14/850,095.
Response filed Apr. 7, 2017, to non-final office action dated Mar. 22, 2017, in U.S. Appl. No. 14/850,095.
Response to Office Action, filed Nov. 1, 2016, in corresponding Japanese Patent Application 2016-515958, including English translation of amended claims.
Response to Office Action, filed Sep. 16, 2016, in connection with U.S. Appl. No. 14/850,095.
Written Opinion dated Nov. 24, 2015, from corresponding PCT application PCT/US2015/049356 filed Sep. 10, 2015.
Response to Final Rejection, filed Sep. 1, 2017, in related U.S. Appl. No. 14/850,095.
Response to Office Action, filed Jul. 25, 2017, in European Application No. 15770712.6.
Office Action dated Feb. 23, 2018, in U.S. Appl. No. 14/850,095, filed Sep. 10, 2015.
Office Action dated Feb. 23, 2018, in U.S. Appl. No. 15/296,183, filed Oct. 18, 2016.
Office Action dated Oct. 5, 2017, in related European Application No. 15770712.6 filed Sep. 10, 2015.
Response to Office Action filed Dec. 4, 2017, in related European Application No. 15770712.6 filed Sep. 10, 2015.
Final Rejection dated Aug. 8, 2018, in U.S. Appl. No. 14/850,095.
Response to Office Action, filed Jun. 22, 2018, in U.S. Appl. No. 14/850,095.
European Search Report and Search Opinion in EP18177601.4, dated Oct. 12, 2018.
Notice of Allowance dated Oct. 25, 2018, in U.S. Appl. No. 14/850,095.
Response to Final Rejection, filed Oct. 8, 2018, in U.S. Appl. No. 14/850,095.
Japanese Office Action dated Dec. 19, 2017, in Japanese Application No. 2017-028336.
Japanese response to office action filed Mar. 16, 2018, in Japanese Application No. 2017-028336.
Response to Office Action filed Feb. 28, 2018 in corresponding U.S. Appl. No. 15/296,183.

* cited by examiner

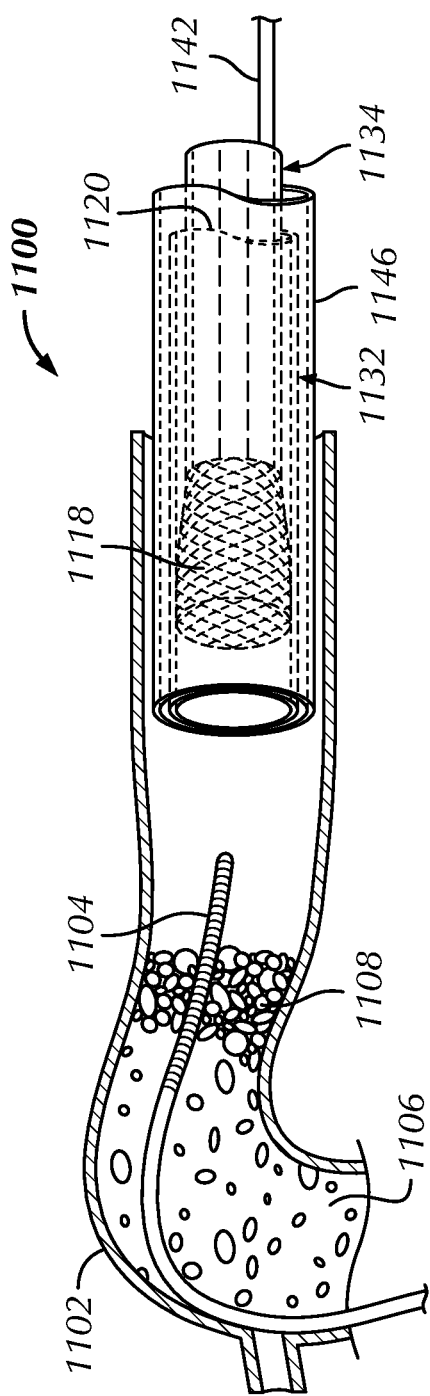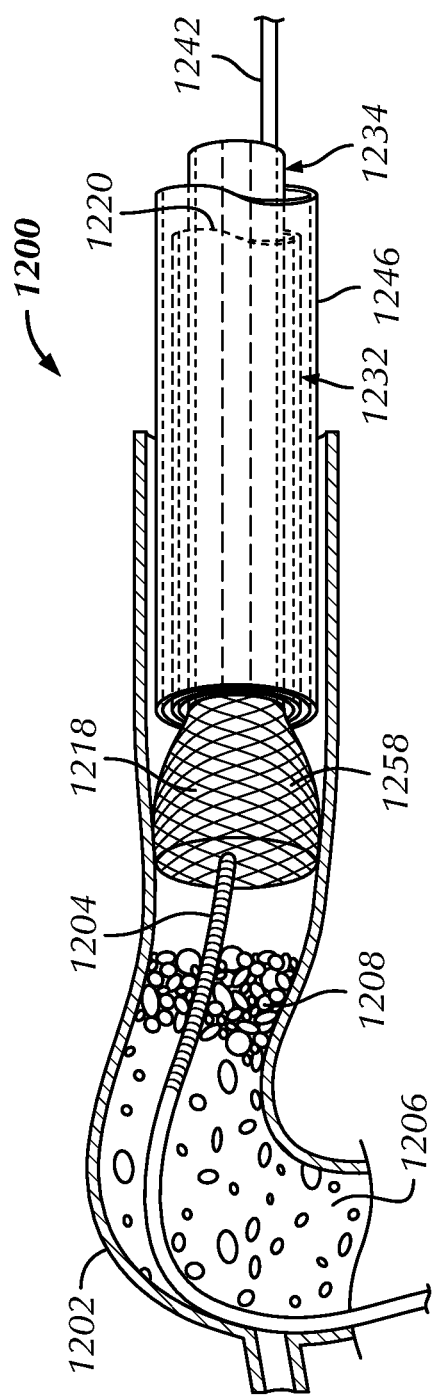
FIG. 11
FIG. 12

GUIDEWIRE CAPTURE

CLAIM OF PRIORITY

This non-provisional patent application claims the benefit of priority under 35 U.S.C. § 119(e) to U.S. Provisional Patent Application Ser. No. 62/048,734, entitled "GUIDEWIRE CAPTURE," filed on Sep. 10, 2014, which is herein incorporated by reference in its entirety.

TECHNICAL FIELD

This patent document relates to the field of surgical instruments for use in treating severe or chronic total occlusions of blood vessels.

BACKGROUND

A severe or chronic total occlusion (CTO) is a vessel blockage that prevents blood flow beyond the occlusion. Chronic total occlusions most often occur in coronary and peripheral arteries and result from atherosclerosis.

A common procedure for treating CTOs is percutaneous transluminal angioplasty. During an angioplasty procedure, access to a desired blood vessel is obtained and a guidewire is introduced into the blood vessel in an antegrade direction. The guidewire is maneuvered into place, including being passed into and through the occlusion, and acts as a guide for positioning subsequent treatment devices (e.g., a balloon catheter and/or a stent catheter) over-the-wire. The guiding function of the guidewire can reduce the risk of vessel trauma (e.g., scraping of a luminal wall at an undesired angle or vessel perforation) by the less flexible and larger diameter treatment devices during advancement.

A failure mode for angioplasty is the inability to successful pass a guidewire through an occlusion and into the true lumen of the blood vessel distal to the occlusion. The occlusion may be composed of dense plaque having a proximal cap that prevents penetration by the guidewire.

OVERVIEW

The present inventors recognize that approaching an occlusion in a retrograde direction from its less dense distal end can allow successful passage of a guidewire into and through the occlusion. After crossing the occlusion, the guidewire can be captured and externalized, allowing it to be exchanged with a new guidewire or used for subsequent introduction of one or more over-the-wire treatment devices.

The inventors further recognize the potential complications for capturing the retrograde-directed guidewire on the proximal side of the occlusion and preventing vessel perforation there. It is this recognition that led to the present assemblies and methods for capturing guidewires advanced through a blood vessel in an opposing, retrograde direction.

A present assembly can include a constraining catheter and a capture catheter, each of which can be inserted through a guide catheter. The constraining catheter can include a first longitudinal member and a tubular member, and the tubular member can be eccentrically coupled with a distal end portion of the first longitudinal member. The capture catheter can include a second longitudinal member and a funnel member, and the funnel member can be eccentrically coupled with a distal end portion of the second longitudinal member. The funnel member can be moved between a collapsed configuration and an expanded configuration through relative movement between the first and second longitudinal members. In the collapsed configuration, at least a portion of the funnel member is disposed within a lumen of the tubular member. In the expanded configuration, this portion of the funnel member projects from an end of the tubular member.

A present method for capturing a retrograde guidewire for exchange or use can include introducing a guide catheter and an assembly into a blood vessel at a location upstream of an occlusion. After the guide catheter is introduced and advanced in an antegrade direction toward a proximal end of the occlusion, the assembly, including a capture catheter and a surrounded constraining catheter, can be introduced into the guide catheter and advanced to its distal end portion. At least a portion of a funnel member of the capture catheter can be deployed from within a tubular member of the constraining catheter through relative movement between a first longitudinal member, eccentrically coupled with the tubular member, and a second longitudinal member, eccentrically coupled with the funnel member. The guidewire, introduced into the blood vessel at a location downstream of the occlusion, can be advanced in a retrograde direction and into and through the funnel member and the tubular member.

The present assemblies and methods provide many advantageous features. The assemblies can be ready for use upon removal from their packaging—a funnel member of a capture catheter can come preloaded within a tubular member of a constraining catheter. The funnel member can be easily deployed adjacent a proximal end of an occlusion using a clinician-operated control mechanism. Upon deployment, the funnel member can include a one-size-fits-all configuration that is expandable against luminal vessel walls of various shapes and sizes. The tubular member can be used as a guide extension post-guidewire capture to help advance a treatment device to the occlusion. The funnel member and the tubular member can include a rapid exchange configuration, which minimizes the length of a guidewire that needs to be advanced out of the blood vessel for handling by a treating clinician and, when used in conjunction with a guide catheter including sidewall perforations, can allow for perfusion blood flow during the guidewire capture procedure.

These and other examples and features of the present assemblies and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present assemblies and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in the present patent document.

FIGS. 11-13 illustrate sequential schematic views of guidewire capture using a present assembly, as constructed in accordance with at least one embodiment.

Figure 1:
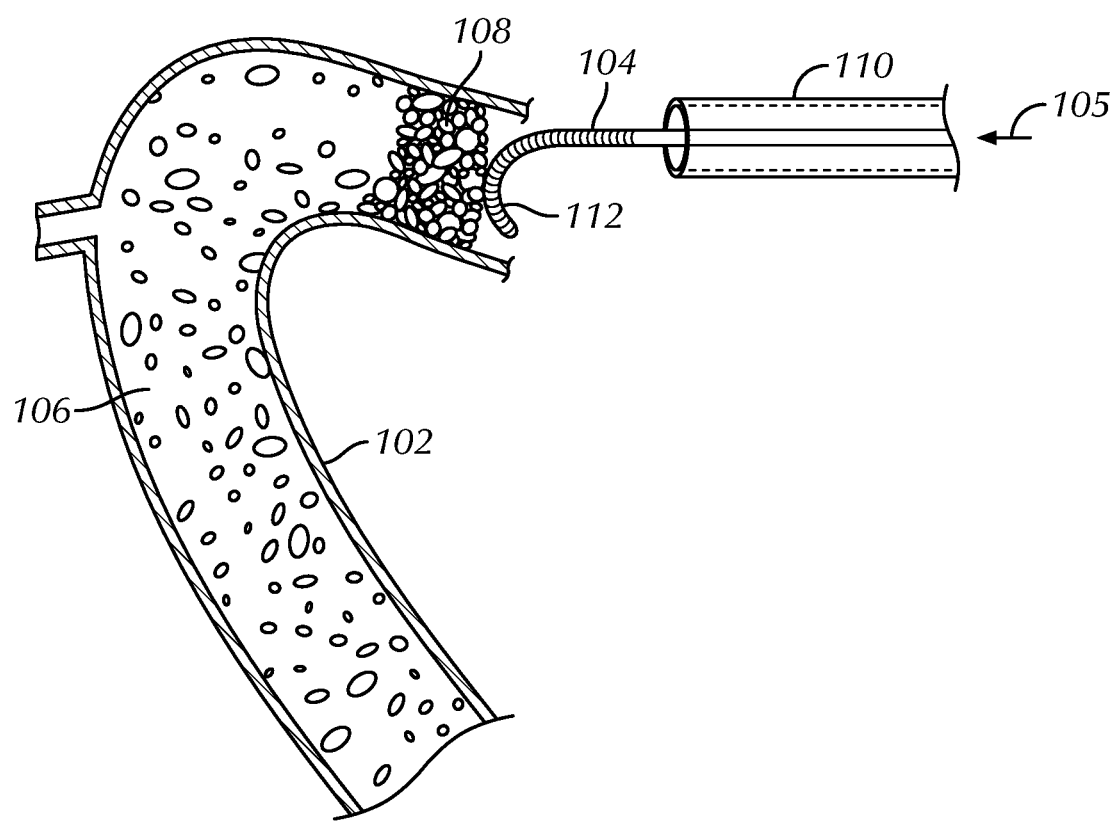
FIG. 1 illustrates a schematic view of a guidewire advanced in an antegrade direction and unable to penetrate a proximal end of an occlusion within a blood vessel.

The drawing figures are not necessarily to scale. Certain features and components may be shown exaggerated in scale or in schematic form and some details may not be shown in the interest of clarity and conciseness.

DETAILED DESCRIPTION

When performing angioplasty procedures using the Seldinger technique, an angioplasty catheter can be introduced into a patient's vascular system by first employing a sharpened hollow needle to penetrate the skin, the underlying muscle tissue, and to enter a selected blood vessel 102. Next, a guidewire 104 can be inserted through the lumen of the hollow needle and made to enter the selected blood vessel 102. The needle can then be stripped off the guidewire 104 leaving the guidewire inside the blood vessel 102. An introducer alone or in combination with a dilator can be fed over the guidewire 104, pushed through the skin, and enter the selected blood vessel 102. The guidewire 104 can be advanced in an antegrade direction 105 to a proximal end of an occlusion 106 within the blood vessel 102 and pushed, or attempted to be pushed, through the occlusion 106.

The occlusion 106 may be at least partially composed of dense plaque forming a proximal cap 108 that prevents penetration by the guidewire 104. If the guidewire 104 is unable to penetrate the proximal cap 108, the dilator can be removed and a support catheter 110 can optionally be advanced into the introducer to a location proximate a distal end 112 of the guidewire 104. The support catheter 110 can provide column strength to the guidewire 104 as a treating clinician urges the guidewire's distal end 112 through the proximal cap 108. Sometimes, even with the assistance of the support catheter, the guidewire 104 is unable to penetrate the proximal cap 108 of the occlusion, as illustrated in FIG. 1.

Figure 3:
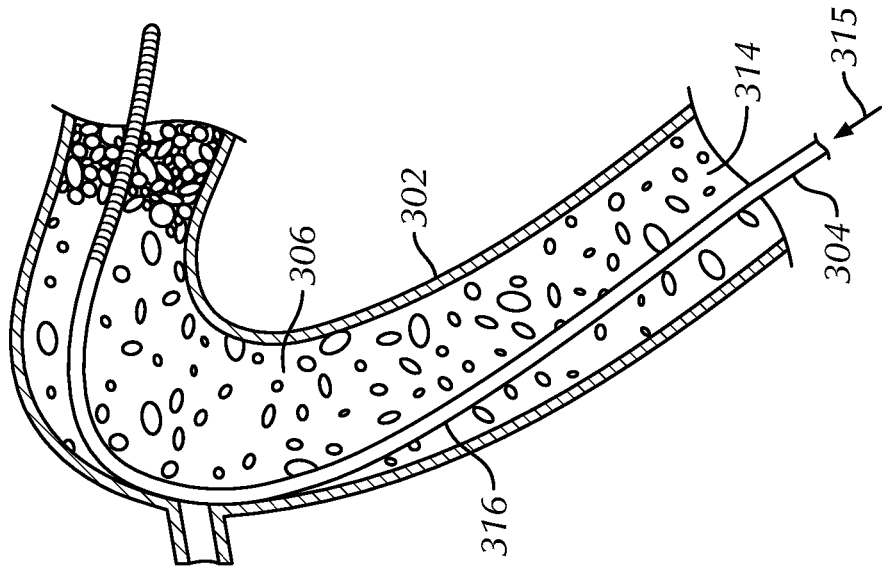
FIG. 3 illustrates a schematic view of a guidewire advanced in a retrograde direction and through an occlusion within a blood vessel.
Figure 2:
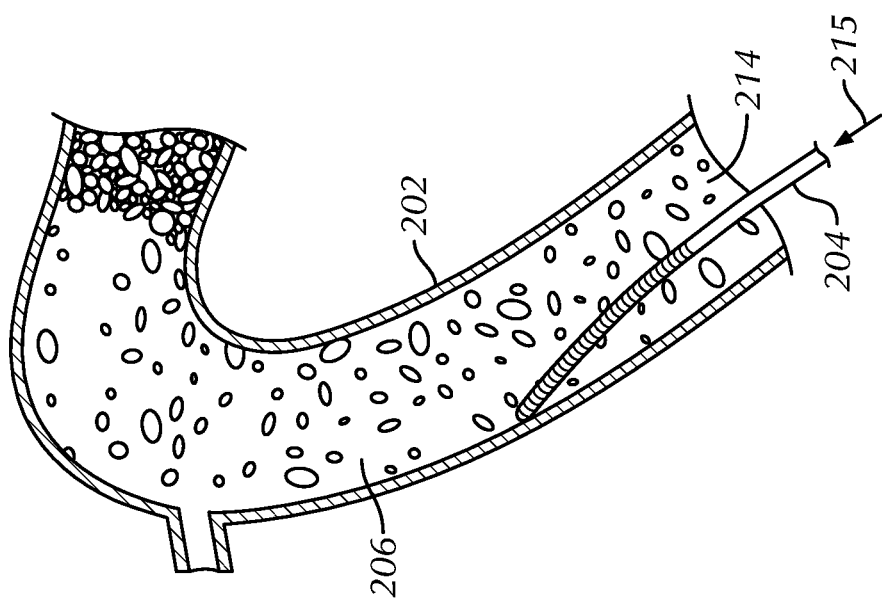
FIG. 2 illustrates a schematic view of a guidewire advanced in a retrograde direction and into a distal end of an occlusion within a blood vessel.

FIGS. 2 and 3 illustrate that by approaching an occlusion 206, 306 within a blood vessel 202, 302 from its less dense distal end 214, 314 and in a retrograde direction 215, 315, a guidewire 204, 304 can be successfully passed into and through the occlusion 206, 306. The guidewire 204, 304 can be placed at the distal end 214, 314 of the occlusion 206, 306 and then advanced into the occlusion from a distal true lumen of the blood vessel 202, 302. If the occlusion 206, 306 cannot be crossed with the guidewire 204, 304 alone, a support catheter (not shown) can be introduced and used to provide column support to the guidewire 204, 304. The guidewire 204, 304 alone or with the help of the support catheter can be maneuvered through the occlusion 206, 306 and create a continuous channel 316 from the distal true lumen to a proximal true lumen of the blood vessel 202, 302.

After crossing the occlusion 206, 306, the guidewire 204, 304 can be captured, externalized and exchanged or used for subsequent introduction of an over-the-wire treatment device. During retrograde procedures, retrieving and exchanging guidewires 204, 304 using a device inserted in an opposing direction can be difficult, time-consuming and frustrating for the treating clinician. Manipulation of existing guidewire snares, for example, is inherently dangerous (e.g., can lead to luminal wall skiving or perforation), unreliable, damaging to the guidewire, and time-consuming.

Figure 4:
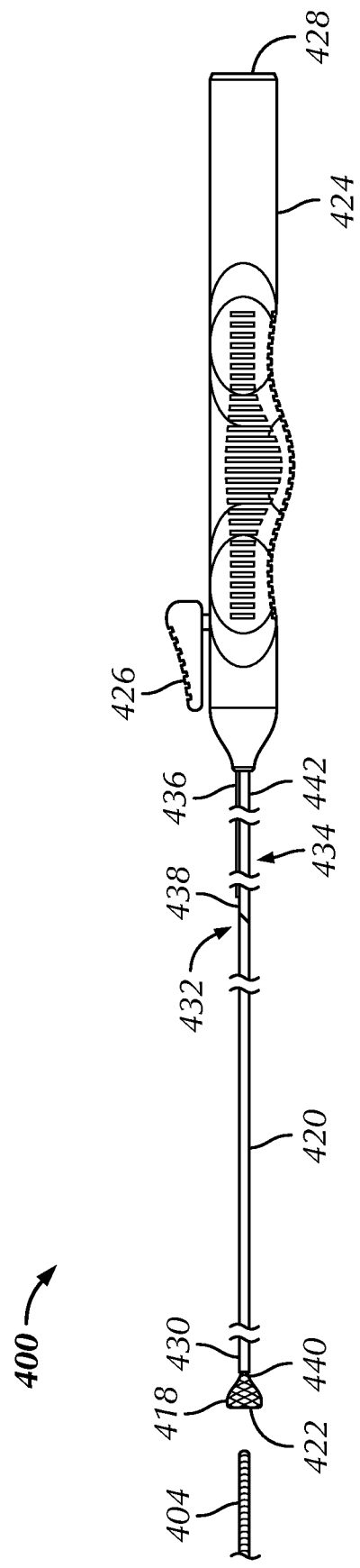
FIG. 4 illustrates a side view of a present assembly, including a constraining catheter, a capture catheter and a control mechanism, for capturing a guidewire advanced in a retrograde direction and into and through an occlusion within a blood vessel, as constructed in accordance with at least one embodiment.

The present assemblies and methods allow for reliably capturing a retrograde guidewire without damage to the guidewire or luminal wall of the blood vessel. After being captured, the guidewire can be externalized allowing the treating clinician to continue with an intervention. It is believed that the assemblies and methods can shorten procedure times and reduce radiation exposure for the treating clinician and the patient. A one-size-fits-all funnel member 418 of an example assembly 400, such as the example illustrated in FIG. 4, expands outward when advanced past a tubular member 420 of the assembly, receives the retrograde directed guidewire 404, and directs the guidewire 404 proximally to the treating clinician. The funnel member 418 can include a distal flaring segment 422 providing an enlarged target area for receiving the guidewire 404. Relative movement between the funnel member 418 and the tubular member 420 can be easily effectuated using a control mechanism 424 including a slide member 426. After being captured, the guidewire 404 can be externalized and exchanged or used for subsequent introduction of over-the-wire treatment devices. The assembly 400 can include a rapid exchange configuration, which minimizes the length of the guidewire 404 that needs to be advanced out of the blood vessel for handling by the treating clinician.

Figure 7:
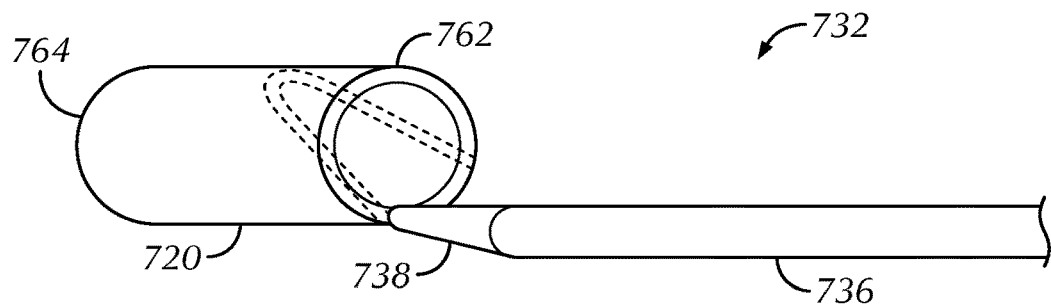
FIG. 7 illustrates a distal end portion of a constraining catheter, as constructed in accordance with at least one embodiment.
Figure 8:
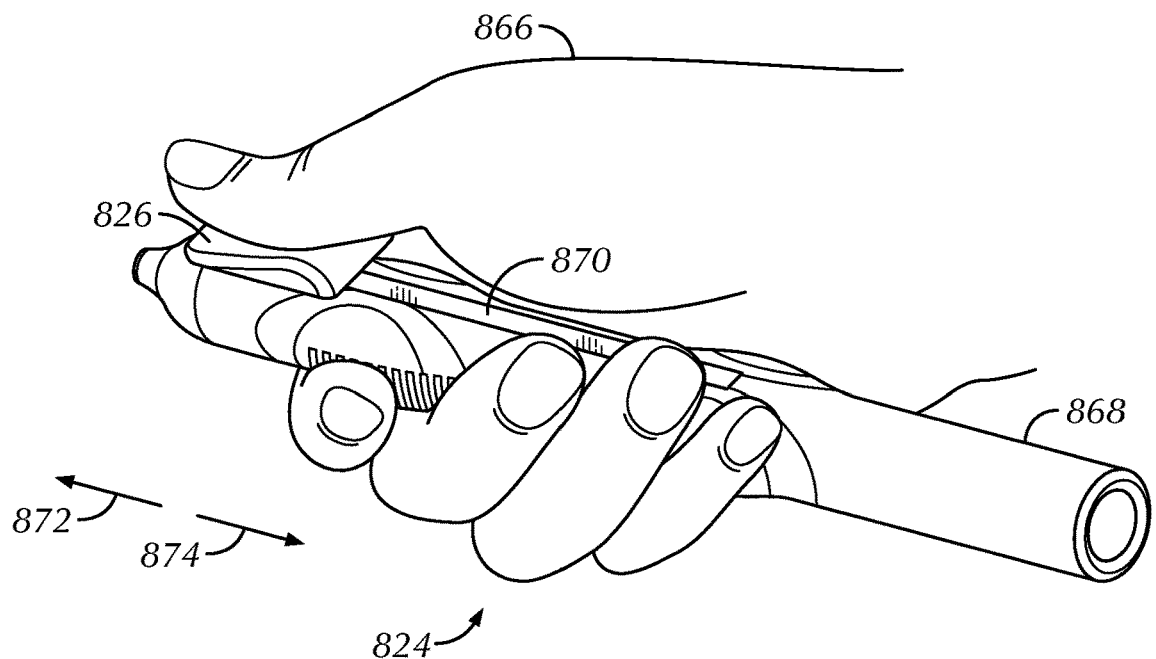
FIG. 8 illustrates a control mechanism operably couplable to a proximal end portion of one or both of the capture catheter or the constraining catheter, as constructed in accordance with at least one embodiment.

The assembly 400 can extend from a proximal end 428 to a distal end 430 and can include a capture catheter 434 (see also FIG. 6), a constraining catheter 432 (see also FIG. 7) and the control mechanism 424 (see also FIG. 8). The constraining catheter 432 can include a first longitudinal member 436 and the tubular member 420. The tubular member 420 can be coupled with a distal end portion 438 of the first longitudinal member 436 and defines a lumen. The capture catheter 434 can include a second longitudinal member 442 and the funnel member 418. The funnel member 418 can be coupled with a distal end portion 440 of the second longitudinal member 442, which extends distal to the distal end portion 438 of the first longitudinal member 436, and, in a distal-to-proximal direction, defines a narrowing passageway. The funnel member 418 can be movable between a collapsed configuration, where at least a portion of the funnel is disposed within the lumen of the tubular member 420, and the expanded configuration illustrated in FIG. 4 for capturing the guidewire 404, where the portion projects from an end of the tubular member 420.

Figure 5:
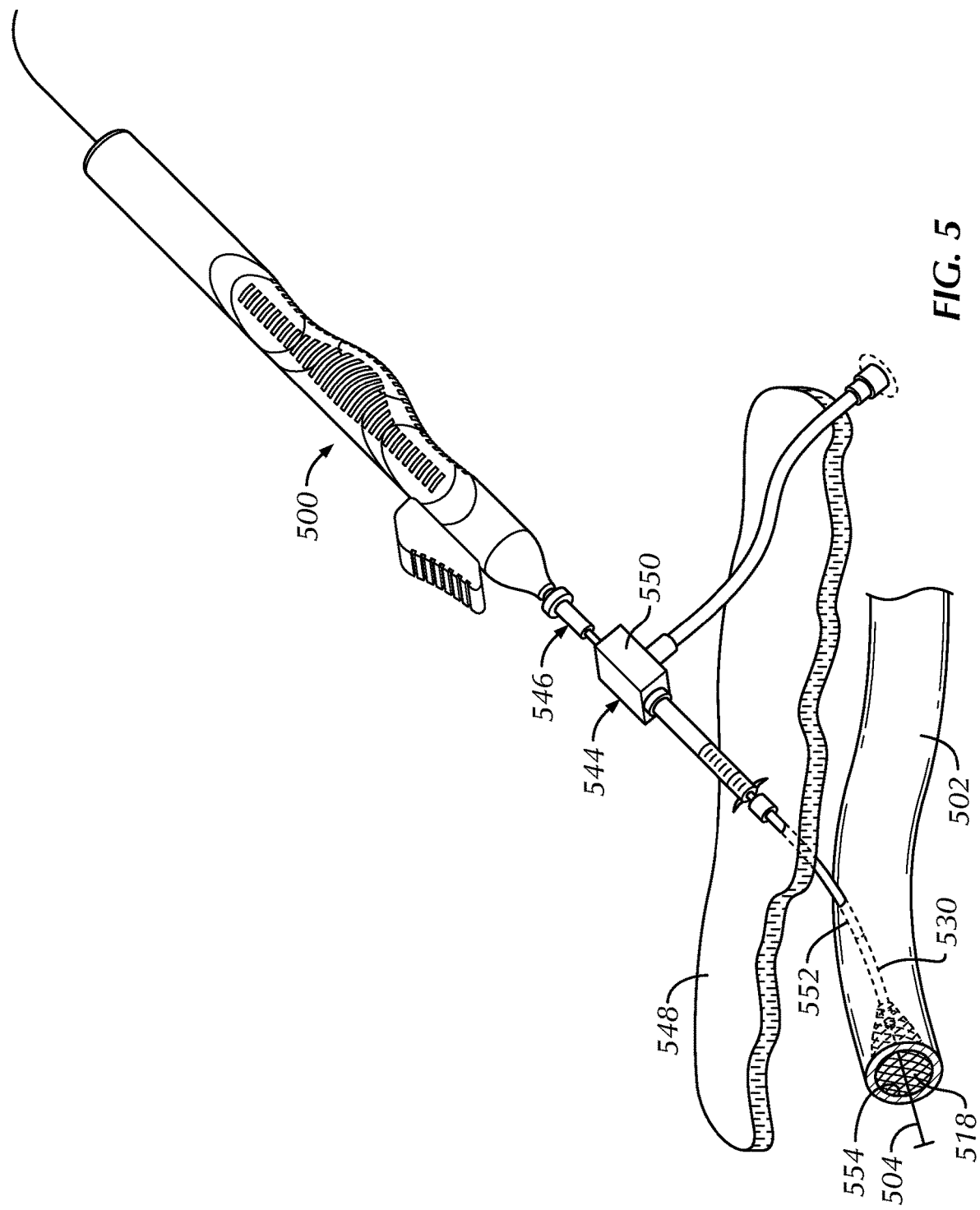
FIG. 5 schematically illustrates a method of using a present assembly for capturing a guidewire advanced in a retrograde direction and into and through an occlusion within a blood vessel, as constructed in accordance with at least one embodiment.

The present assembly 500 can be inserted into a selected blood vessel 502 at a location upstream of an occlusion and advanced to a proximal end of the occlusion (not shown) using the Seldinger technique, an introducer 544 and a guide catheter 546. Prior to the stage of the insertion procedure illustrated in FIG. 5, the Seldinger technique of inserting a hollow needle into the blood vessel 502 has already been accomplished and a guidewire 504 has been inserted through the needle and gently advanced to a desired depth within the blood vessel 502. Following that, the hollow needle has been carefully slipped off the guidewire 504 at its proximal end while the guidewire was held in place. At this point, the introducer 544 alone or in combination with a dilator was fed over the guidewire 504, pushed through the skin 548, and entered the selected blood vessel 502. The dilator, if present, was then removed from the introducer 544.

The guide catheter 546 was introduced into the blood vessel 502 by inserting its distal end 552 through an opening of a hub 550 of the introducer 544 and advanced in an antegrade direction toward the proximal end of the occlusion. The guide catheter 546 extends from a proximal end to the distal end 552 and defines a guide lumen through which the assembly 500 can be guided.

With the guide catheter 546 positioned within the blood vessel 502, the distal end 530 of the assembly 500 was introduced through the guide lumen and advanced into the vessel to the proximal end of the occlusion. In some examples, it can be preferable to introduce the assembly 500 into the blood vessel 502 with the guidance of the guidewire 504. In such examples, since the guidewire 504 is inserted before the assembly 500, it can be preferable to provide a lumen within the captivation and capture catheters of the assembly 500 through which the guidewire 504 can pass. When the funnel member of the capture catheter is in its collapsed configuration, the funnel member defines a guidewire-following aperture. Once the funnel member 518 has been placed in the blood vessel 502 in which it is to capture a second, retrograde guidewire (not shown), the funnel member 518 can be deployed to its expanded configuration and the guidewire 504 can be removed. In this expanded configuration, it is preferable that a portion of the funnel member 518 expands to a size at which its outer perimeter bears against the circumferential luminal wall 554 of the blood vessel 502.

Figure 6:
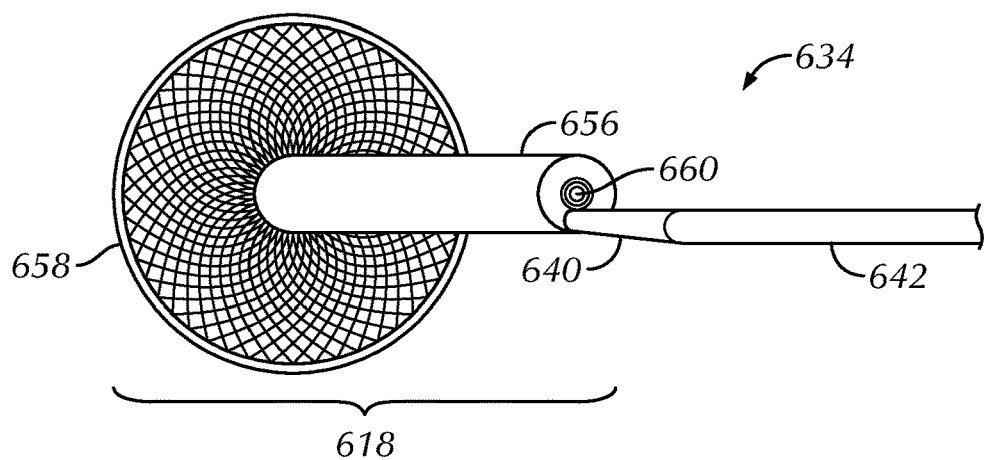
FIG. 6 illustrates a distal end portion of a capture catheter, as constructed in accordance with at least one embodiment.

FIG. 6 illustrates a distal end portion of a capture catheter 634, including a second longitudinal member 642 and a funnel member 618. The funnel member 618 can be eccentrically coupled with a distal end portion 640 of the second longitudinal member 642. In an example, the funnel member 618 can be fused or bonded to a second longitudinal member in the form of an elongated hypotube, ribbon or wire. In various examples, a length of the funnel member 618 is less than a length of the second longitudinal member 642.

The funnel member 618 can be generally conical in shape and can include a proximal tubular segment 656 and a distal flaring segment 658. The tubular segment 656 can include a lumen 660 configured to slide over a guidewire during insertion within a blood vessel and receive a retrograde guidewire during a capturing procedure. The flaring segment 658 can be configured to have a collapsed configuration for insertion purposes and an expanded configuration for guidewire capture. The flaring segment 658 can be disposed within a tubular member of a constraining catheter (FIG. 7) when in the collapsed configuration and can assume the expanded configuration upon being projected from the tubular member through actuation of a control mechanism (FIG. 8). When in the expanded configuration, the flaring segment 658 can have a diameter that is greater than the diameter of the tubular member in which it is initially housed.

The flaring segment 658 can include a self-expandable material, which can undergo deformations when under the influence of force and then spring back to its original shape after the force is removed. If, for example, the second longitudinal member 642 urges the flaring segment 658 out of the tubular member (thereby allowing the flaring segment to assume a relaxed state), the free end of the flaring segment 658 will assume the expanded configuration illustrated in FIG. 6. In this condition, the free end of the flaring segment 658 will engage against the luminal wall of a blood vessel and will direct a guidewire with which it comes into contact into the tubular segment 656. In an example, the flaring segment 658 includes a dual-layer braided member that permits blood flow. The advantage of having blood flow through the flaring segment 658 is that downstream cellular and physiologic needs can be at least partially met during the guidewire capture procedure. In another example, the flaring segment 658 includes an inflatable member such as a helically-wound balloon.

The constraining catheter 732 illustrated in FIG. 7 includes a first longitudinal member 736 and a tubular member 720. The tubular member 720 extends from a proximal end portion 762 to a distal end portion 764 and defines a continuous lumen 766. In various examples, a length of the tubular member 720 is less than a length of the first longitudinal member 736. The proximal end portion 762 can include a skived entry (shown in phantom) and the distal end portion 764 can be comparatively softer than the proximal end portion. The tubular member 720 can be loaded with barium sulfate or other suitable material to provide radiopacity. The inner surface of the tubular member 720 can be coated with silicone or other polymer to provide a slippery surface. The tubular member 720 can be formed of a braided or coiled support member for increased compression strength. An outer coating of plastic can be added around the braided support member using a heat shrink or similar manufacturing technique to define the tubular member 720.

The tubular member 720 can be eccentrically coupled with the distal end portion 738 of the first longitudinal member 736. It should be appreciated that this eccentric coupling can provide leverage for facilitating manipulation of the tubular member 720 by way of the first longitudinal member 736. The first longitudinal member 736 can be coupled with the tubular member 720 by inserting it into a receiving hole and affixing it therein by, for example, gluing, pressure fitting, shrink fitting, or the like. Alternatively, the tubular member 720 can be molded directly onto the first longitudinal member 736.

A control mechanism 824 can be operably couplable with a proximal end portion of one or both of a capture catheter (FIG. 6) or a constraining catheter (FIG. 7) to move a funnel member of the capture catheter between collapsed and expanded configurations. Actuation of the control mechanism 824 can cause relative movement between the first and second longitudinal members of the constraining and capture catheters, respectively; resulting in a flaring segment of the funnel member being projected from the tubular member of the constraining catheter.

The control mechanism 824 illustrated in FIG. 8 includes a housing 868 positionable outside a patient for manipulation by a treating clinician's hand 866. The housing 868 can include a longitudinal slot 870 allowing a thumb-operated slide member 826 to move along a linear path. The slide member 826 can be operably coupled with the second longitudinal member so that distal movement 872 of the slide member 826 results in distal movement of the funnel member and proximal movement 874 of the slide member 826 results in proximal movement of the funnel member. In this arrangement, the funnel member can be ejected from the tubular member through advancement (or distal movement 872) of the second longitudinal member. In an alternate arrangement, the slide member 826 can be operably coupled with the first longitudinal member so that movement of the slide member 826 results in movement of the tubular member. In this alternative arrangement, the funnel member can be ejected from the tubular member through retraction (or proximal movement 874) of the first longitudinal member.

To avoid accidental, premature ejection of the funnel member from the tubular member, a locking arrangement can be used to couple the slide member 826 to the housing 868 to prevent relative movement between these two parts until the lock is released. The locking arrangement can, for example, include a locking pin passing transversely through the longitudinal slot 870 to prevent inadvertent movement of the slide member 826.

Figure 9:
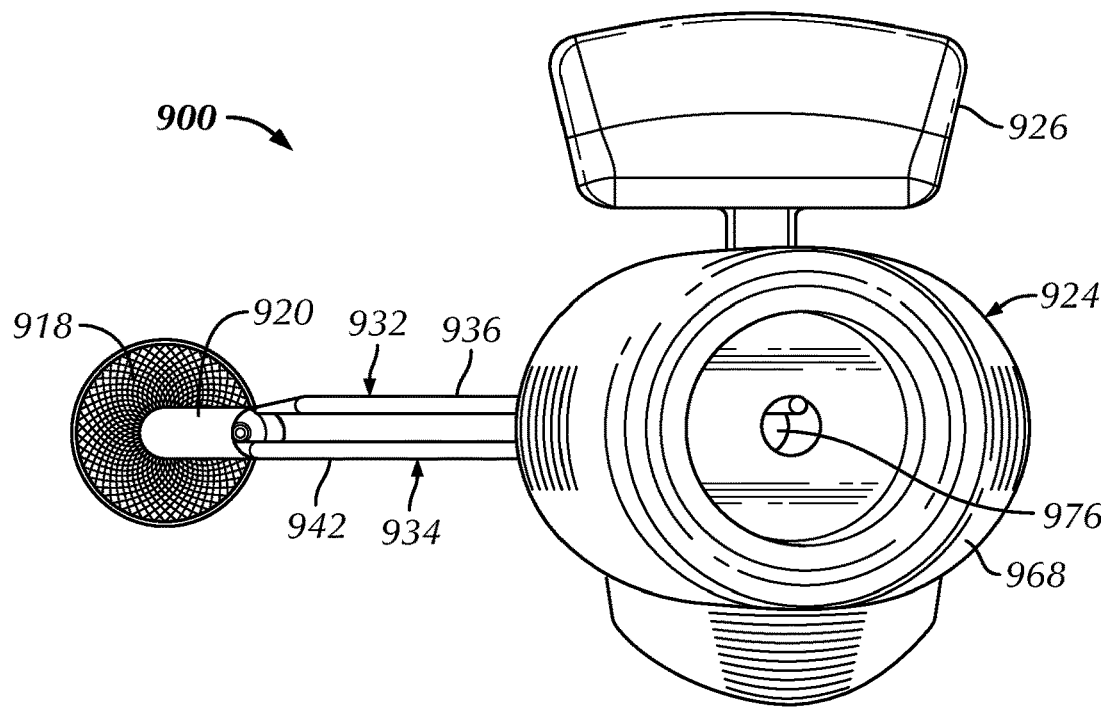
FIG. 9 illustrates a rear view of a present assembly for capturing a guidewire advanced in a retrograde direction and into and through an occlusion within a blood vessel, as constructed in accordance with at least one embodiment.
Figure 10:
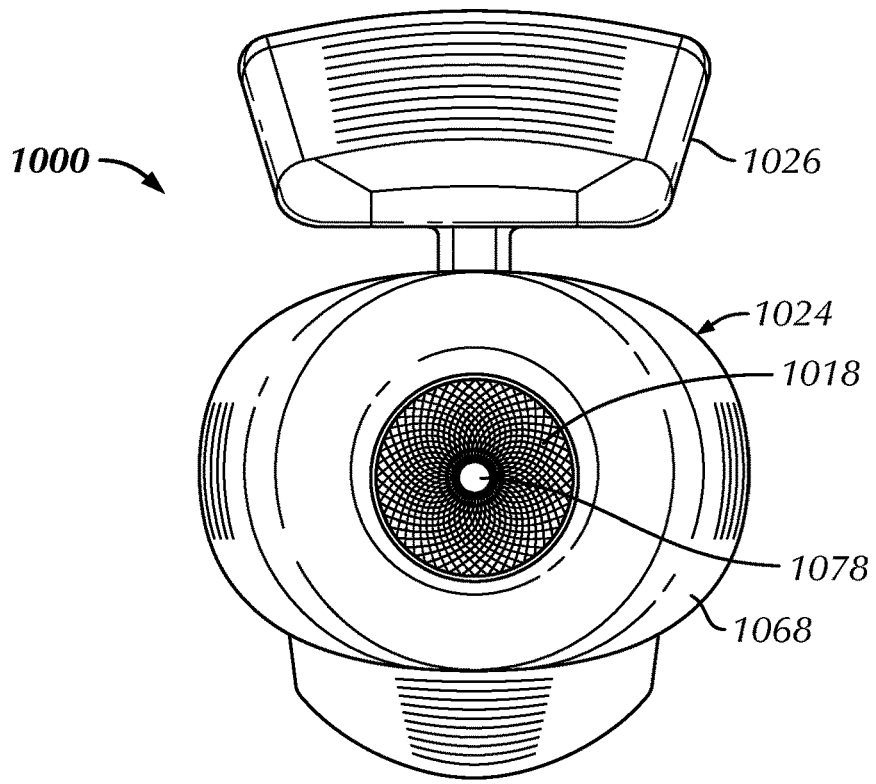
FIG. 10 illustrates a front view of a present assembly for capturing a guidewire advanced in a retrograde direction and into and through an occlusion within a blood vessel, as constructed in accordance with at least one embodiment.
Figure 13:
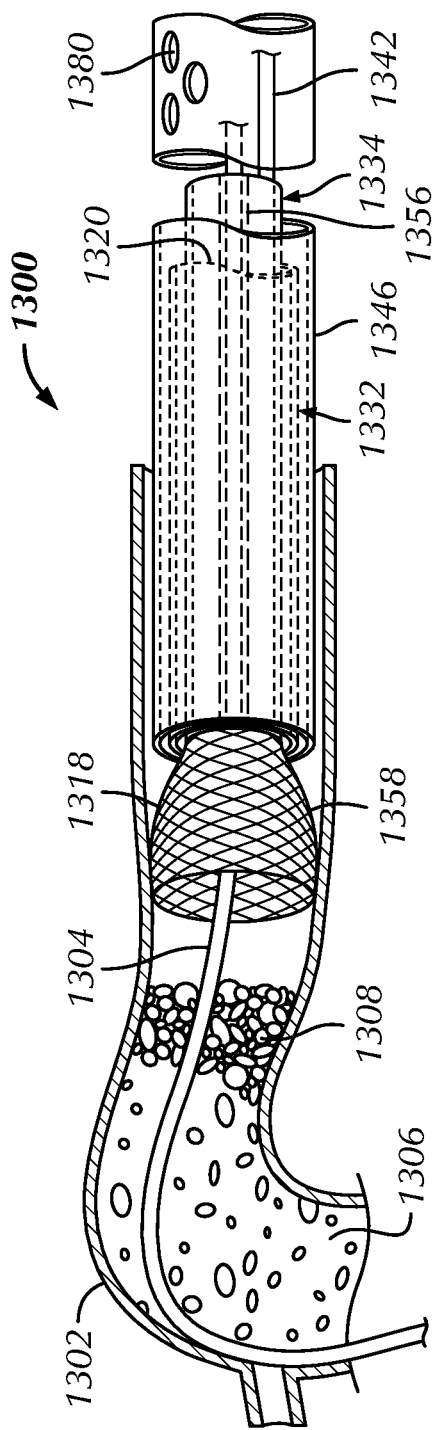
Figure 14:
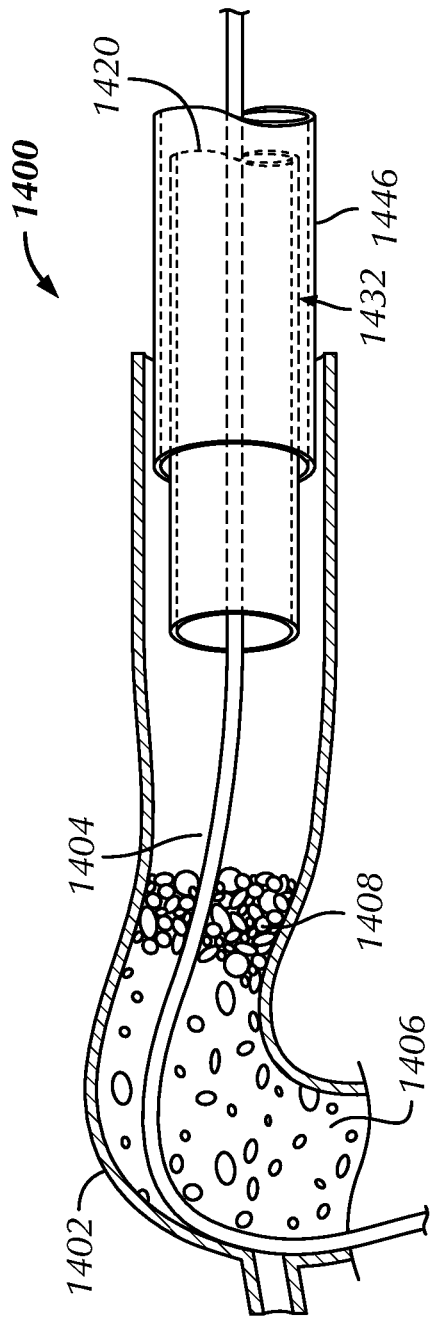
FIG. 14 illustrates a schematic view of a constraining catheter left in place within a blood vessel for delivery of a treatment device following removal of a capture catheter.

FIGS. 9 and 10 respectively illustrate rear and front views of an assembly 900, 1000 for capturing a guidewire advanced in a retrograde direction, including a constraining catheter 932, a capture catheter 934 and a control mechanism 924, 1024. The constraining catheter 932 can include a first longitudinal member 936 and a tubular member 920. The capture catheter 934 can include a second longitudinal member 942 and a funnel member 918, 1018. The control mechanism 936 can include a housing 968, 1068 having a lumen 976 on its proximal end and a slide member 926, 1026. FIG. 9 shows the rapid exchange configuration of the constraining 932 and capture 934 catheters, as well as a prepackaged arrangement of the catheters, with the capture catheter 934 at least partially disposed within the constraining catheter 932. FIG. 10 shows the narrowing passageway encountered by the retrograde guidewire as it approaches the assembly 900. An axial guidewire passageway 978, 1078 extending to a treating clinician outside a patient's body can be defined by the funnel member 918, 1018, the tubular member 920 and the lumen 976 of the control mechanism 936.

After a retrograde guidewire 1104, 1204, 1304, 1404 successfully passes into and through a proximal cap 1108, 1208, 1308, 1408 of an occlusion 1106, 1206, 1306, 1406, the guidewire 1104, 1204, 1304, 1404 can be captured using a present assembly 1100, 1200, 1300, 1400 and externalized and exchanged or used for subsequent introduction of an over-the-wire treatment device, as sequentially illustrated in FIGS. 11-14.

A guide catheter 1146, 1246, 1346, 1446 can be introduced into a blood vessel 1102, 1202, 1302, 1402 at a location upstream of the occlusion 1106, 1206, 1306, 1406 and advanced in an antegrade direction toward the proximal cap 1108, 1208, 1308, 1408. A contrast agent can be injected into the guide catheter 1146 to confirm its distal position. Distal portions of the assembly 1100, including a constraining catheter 1132 and a capture catheter 1134, can be introduced into the guide catheter 1146 and advanced to or beyond its distal end. A tubular member 1120 of the constraining catheter can protect a funnel member 1118 of the capture catheter during insertion into the guide catheter and blood vessel.

The funnel member 1218 of the capture catheter 1234 can emerge from the lumen of the tubular member 1220 of the constraining catheter 1232. Upon exiting the tubular member 1220 and the guide catheter 1246, a flaring segment 1258 of the funnel member can assume an expanded configuration providing a wide mouth goal for the approaching guidewire 1204. In the expanded configuration, it is preferable that the flaring segment 1258 bears against the luminal wall of the blood vessel 1206, thereby providing assurance that as the guidewire 1204 and the capture catheter 1234 approach one another, the guidewire will eventually make contact with the funnel member and be directed into the catheter 1234. The funnel member 1218 can be deployed by distally advancing a second longitudinal member 1142, 1242, 1342 coupled with the funnel member or by proximally withdrawing a first longitudinal member coupled with the tubular member 1120, 1220, 1320, each of which can be actuated by a control mechanism (not shown) located outside a patient's body and operably coupled with proximal portions of the longitudinal members.

The guidewire 1304 can be pushed through flaring segment 1358 of the funnel member 1318 and into a tubular segment 1356 of the funnel member. Pushing the guidewire 1304 further allows its distal tip to travel through the tubular member 1320 of the constraining catheter to the outside of the patient's body, allowing the treatment procedure to be continued from the upstream side of the occlusion. One or more perforations 1380 in a sidewall of the guide catheter 1346 can allow blood to flow from an upstream vessel location, through the guide catheter, tubular member 1320 and tubular segment 1356, and out the flaring segment 1358 to facilitate distal vessel perfusion. With distal portions of the guidewire 1304 projecting outside the body, the capture catheter 1334 can be withdrawn from the guide catheter 1346, leaving the constraining catheter 1332 in place.

A new catheter, such as an angioplasty balloon catheter, can then be guided along the guidewire 1404 that has been captured and through the tubular member 1420 of the constraining catheter 1432 to the occlusion 1406 for treatment, or the captured guidewire 1404 can be withdrawn and a new guidewire can be advanced through the guide catheter 1446 and tubular member 1420 to the occlusion. In both instances, the tubular member 1420 can act as a guide catheter extension to provide a guide lumen extending beyond the distal end of the guide catheter 1446. The tubular member 1420 can have an outer diameter less than the inner diameter of the guide catheter 1446 so that it can be slidably disposed and an inner diameter sufficiently large to permit passage of the angioplasty balloon catheter therethrough. In various examples, the inner diameter of the tubular member 1420 is not more than one French size smaller than the inner diameter of the guide catheter 1446.

Figure 15:
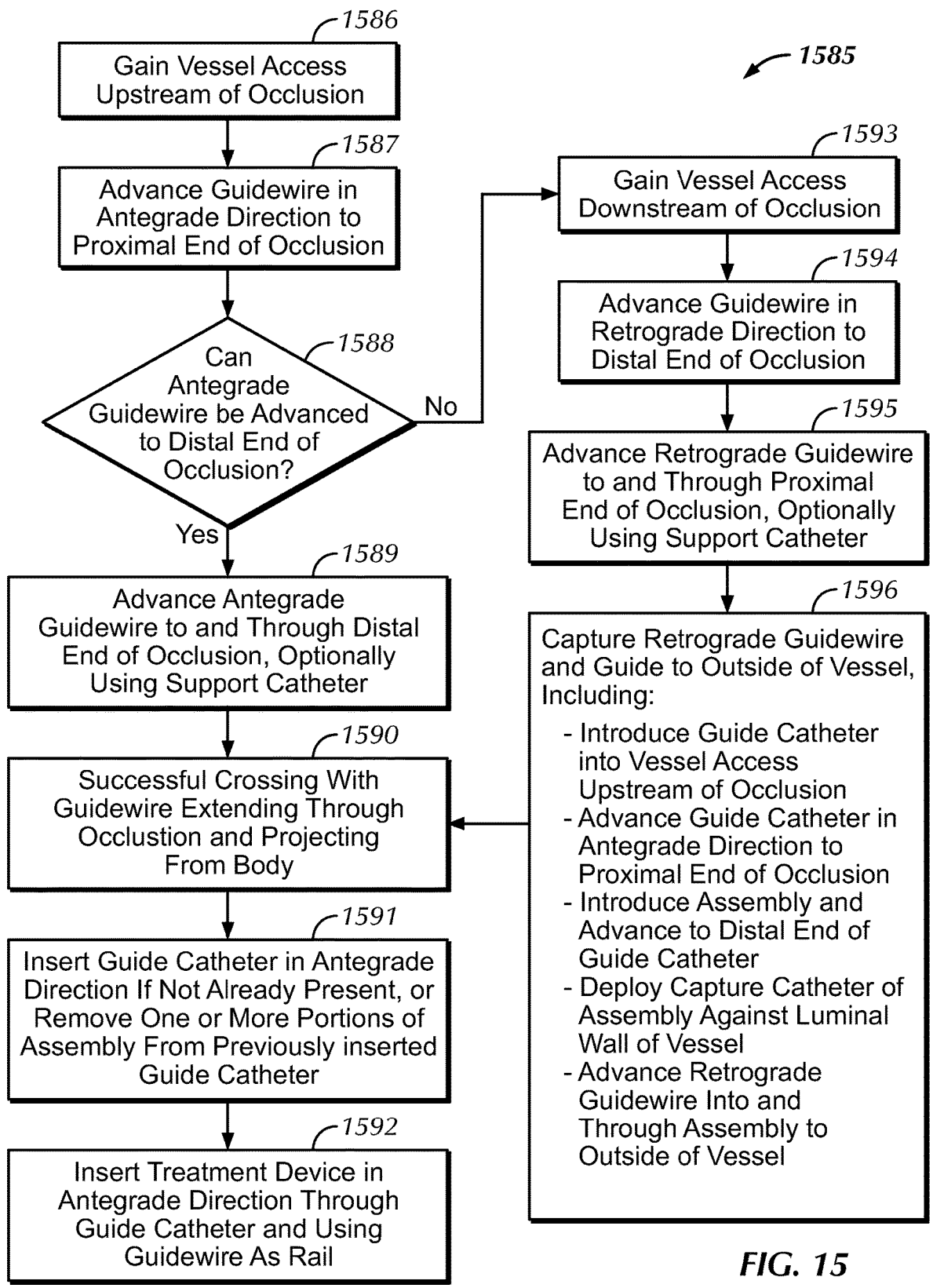
FIG. 15 illustrates a flowchart of steps for capturing a guidewire advanced in a retrograde direction and into and through an occlusion within a blood vessel, as constructed in accordance with at least one embodiment.

With the availability of the present assemblies at hand, FIG. 15 illustrates a flowchart 1585 of steps that a treating clinician can follow when attempting to cross an occlusion within a blood vessel.

At step 1586, access to the blood vessel at a location upstream of the occlusion can be obtained by employing a sharpened hollow needle to penetrate the skin, the underlying muscle tissue, and to enter the selected blood vessel. Next, at step 1587, a first guidewire can be inserted through the lumen of the hollow needle, made to enter the blood vessel, and advanced in an antegrade direction to a proximal end of the occlusion. The needle can then be stripped off the first guidewire, leaving the guidewire inside the blood vessel. An introducer alone or in combination with a dilator can be fed over the first guidewire.

At step 1588, the treating clinician can attempt to advance a distal end of the first guidewire into and through the occlusion. If the occlusion can be penetrated by the first guidewire from its proximal end, the treating clinician can advance the guidewire through the occlusion, optionally with the help of a support catheter, and then move to steps 1590-1592. If the occlusion cannot be penetrated from its proximal end, the treating clinician can move to steps 1593-1596 before proceeding to steps 1590-1592.

Assuming the treating clinician cannot penetrate the occlusion's proximal end using the first guidewire, access to the blood vessel can be obtained at a location downstream of the occlusion in a similar manner to step 1586; then, at step 1594, a second guidewire can be made to enter the blood vessel and advanced in a retrograde direction to a distal end of the occlusion. An introducer alone or in combination with a dilator can be fed over the second guidewire. At step 1595, the second guidewire can be further advanced in the retrograde direction into and through the occlusion, optionally with the help of a support catheter. The second guidewire can be captured on the proximal side of the occlusion and guided outside the vessel at step 1596 using the present assemblies. The present assemblies can use the first guidewire as a rail for guidance to the proximal side of the occlusion.

At step 1590, one of the first and second guidewires will have crossed the occlusion and a portion of such guidewire will project outside the blood vessel. If the first guidewire crosses the occlusion, a proximal end portion of the first guidewire will project from the vessel. If the second guidewire crosses the occlusion, a distal end portion of the second guidewire will project from the vessel and can optionally be replaced with a new guidewire. If not already present, a guide catheter can be guided over the in situ guidewire, or a capture catheter of the present assemblies can be removed from a previously inserted guide catheter at step 1591. Finally, at step 1592, one or more treatment devices can be advanced in an antegrade direction through the guide catheter and use the in situ guidewire as a rail.

Closing Notes:

The present assemblies and methods can be used by a treating clinician to reliably capture a retrograde guidewire in an efficient manner, thereby shortening procedure times and reducing radiation exposure for the treating clinician and the patient. A one-size-fits-all funnel member of the assemblies expands outward when projected from an end of a tubular member, receives the retrograde guidewire, and directs the guidewire proximally toward the treating clinician. The funnel member can include a distal flaring segment providing an enlarged target area for receiving the retrograde guidewire. Deployment of the funnel member from the tubular member can be easily achieved using a clinician-operated control mechanism. After being captured, the retrograde guidewire can be externalized and exchanged or used for subsequent introduction of over-the-wire treatment devices. The funnel and tubular members can include a rapid exchange configuration, which minimizes the length of guidewire that needs to be advanced out of the blood vessel and handled by the treating clinician.

The above Detailed Description includes references to the accompanying drawings, which form a part of the Detailed Description. The Detailed Description should be read with reference to the drawings. The drawings show, by way of illustration, specific embodiments in which the present assemblies and methods can be practiced. These embodiments are also referred to herein as "examples."

The above Detailed Description is intended to be illustrative, and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, an assembly for capturing a retrograde guidewire advanced through a blood vessel can comprise a constraining catheter and a capture catheter. The constraining catheter can include a first longitudinal member and a tubular member defining a lumen. The tubular member can be coupled with a distal end portion of the first longitudinal member. The capture catheter can include a second longitudinal member and a funnel member. The funnel member can be coupled with a distal end portion of the second longitudinal member and, in a distal-to-proximal direction, can define a narrowing passageway. The funnel member can be moved between a collapsed configuration, where at least a portion of the member is disposed within the lumen of the tubular member, and an expanded configuration for capturing the guidewire, where the portion of the member projects from an end of the tubular member.

In Example 2, the assembly of Example 1 can optionally be configured such that the tubular member is eccentrically coupled with the distal end portion of the first longitudinal member.

In Example 3, the assembly of any one or any combination of Examples 1 and 2 can optionally be configured such that the funnel member is eccentrically coupled with the distal end portion of the second longitudinal member.

In Example 4, the assembly of any one or any combination of Examples 1-3 can optionally be configured such that the lumen of tubular member has an inner diameter and the portion of the funnel member, when in the expanded configuration, has an outer diameter greater than the inner diameter.

In Example 5, the assembly of any one or any combination of Examples 1-4 can optionally be configured such that the portion of the funnel member, when in the collapsed configuration, has a smaller cross-sectional area than that of the lumen of the tubular member and, when in the expanded configuration, has a larger cross-sectional area than that of the lumen.

In Example 6, the assembly of any one or any combination of Examples 1-5 can optionally be configured such that the funnel member is generally conical in shape.

In Example 7, the assembly of any one or any combination of Examples 1-6 can optionally be configured such that a proximal portion of the funnel member includes a tubular segment and a distal portion of the funnel member includes a flaring segment.

In Example 8, the assembly of Example 7 can optionally be configured such that the tubular segment includes a lumen configured to slide over a guidewire at least partially positioned in the blood vessel.

In Example 9, the assembly of any one or any combination of Examples 7 or 8 can optionally be configured such that the flaring segment includes a multi-layer braided member.

In Example 10, the assembly of any one or any combination of Examples 1-9 can optionally be configured such that the distal end portion of the second longitudinal member is extendable distally of the distal end portion of the first longitudinal member.

In Example 11, the assembly of any one or any combination of Examples 1-10 can optionally be configured such that a length of the tubular member is less than a length of the first longitudinal member, and a length of the funnel member is less than a length of the second longitudinal member.

In Example 12, the assembly of any one or any combination of Examples 1-11 can optionally be configured such that the first and second longitudinal members include an elongated hypotube, ribbon or wire.

In Example 13, the assembly of any one or any combination of Examples 1-12 can optionally be configured such that an intermediate portion, between a proximal end portion and the distal end portion, of one or both of the first longitudinal member or the second longitudinal member includes an arcuate cross-sectional shape configured to cradle the guidewire.

In Example 14, the assembly of any one or any combination of Examples 1-13 can optionally be configured such that a transition between the distal end portion of the first longitudinal member and a proximal end portion of the tubular member includes an angled or skived opening.

In Example 15, the assembly of any one or any combination of Examples 1-14 can optionally further comprise a control mechanism configured to move the funnel member between the collapsed configuration and the expanded configuration.

In Example 16, the assembly of Example 15 can optionally be configured such that the control mechanism includes a slide member operably coupled with a proximal end portion of the first longitudinal member or a proximal end portion of the second longitudinal member.

In Example 17, the assembly of Example 16 can optionally be configured such that the control mechanism includes a locking mechanism to inhibit movement of the slide member.

In Example 18, the assembly of any one or any combination of Examples 1-17 can optionally further comprise a guide catheter surrounding portions of the constraining catheter and the capture catheter.

In Example 19, the assembly of Example 18 can optionally be configured such that a sidewall of the guide catheter includes one or more perforations.

In Example 20, the assembly of any one or any combination of Examples 18 or 19 can optionally be configured such that a diameter of the lumen of the tubular member is not more than one French size smaller than a lumen of the guide catheter.

In Example 21, the assembly of any one or any combination of Examples 18-20 can optionally be configured such that an outer diameter of the tubular member is less than a diameter of the lumen of the guide catheter.

In Example 22, a method for capturing a retrograde guidewire for exchange or use can comprise introducing a guide catheter and an assembly into a blood vessel at a location upstream of an occlusion. After the guide catheter is introduced and advanced in an antegrade direction toward a proximal end of the occlusion, the assembly can be introduced into a proximal end portion of the guide catheter and advanced to its distal end portion. At least a portion of an expandable member of the assembly can be deployed and project beyond the distal end portion of the guide catheter. The guidewire, introduced into the blood vessel at a location downstream of the occlusion, can be advanced in a retrograde direction toward and through the occlusion and into and through the expandable member.

In Example 23, the method of Example 22 can optionally be configured such that introducing the assembly into the proximal end portion of the guide catheter includes introducing a capture catheter and a surrounding constraining catheter into the proximal end portion of the guide catheter.

In Example 24, the method of Example 23 can optionally be configured such that deploying at least the portion of the expandable member includes deploying at least a portion of a funnel member of the capture catheter from a tubular member of the constraining catheter.

In Example 25, the method of Example 24 can optionally be configured such that deploying at least the portion of the funnel member of the capture catheter from the tubular member of the constraining catheter includes actuating relative movement between a first longitudinal member eccentrically coupled with the tubular member and a second longitudinal member eccentrically coupled with the funnel member.

In Example 26, the method of Example 25 can optionally be configured such that actuating relative movement between the first and second longitudinal members includes selectively displacing a slide member of a control mechanism coupled within a proximal end portion of one or both of the first and second longitudinal members.

In Example 27, the method of any one or any combination of Examples 24-26 can optionally be configured such that advancing the assembly to the distal end portion of the guide catheter includes allowing blood flow through each of one or more perforations in a sidewall of the guide catheter, the tubular member of the constraining catheter, and the funnel member of the capture catheter.

In Example 28, the method of any one or any combination of Examples 24-27 can optionally be configured such deploying at least the portion of the funnel member of the capture catheter from within the tubular member of the constraining catheter includes allowing the portion of the funnel member to expand and bear against a luminal wall of the blood vessel.

In Example 29, the method of any one or any combination of Examples 24-28 can optionally further comprise withdrawing the capture catheter from the guide catheter, leaving the constraining catheter in place, and advancing a distal end portion of the tubular member beyond the distal end portion of the guide catheter.

In Example 30, the method of Example 29 can optionally further comprise introducing a treatment device into the guide catheter and, using the guidewire as a rail, advancing the treatment device in the antegrade direction along the first longitudinal member, through an angled opening of the tubular member, and beyond the distal end of the tubular member to the occlusion.

In Example 31, the method of any one or any combination of Examples 22-30 can optionally further comprise introducing a support catheter into the blood vessel at the location downstream of the occlusion and over the guidewire; and wherein advancing the guidewire in the retrograde direction toward and through the occlusion includes using the support catheter.

In Example 32, the method of any one or any combination of Examples 22-31 can optionally be configured such that advancing the guidewire toward and through the occlusion includes creating a continuous channel between proximal and distal ends of a CTO.

In Example 33, the method of any one or any combination of Examples 22-32 can optionally further comprise subsequent to advancing the assembly to the distal end portion of the guide catheter, injecting contrast media to confirm when a distal end portion of the assembly is located proximate the proximal end of the occlusion.

In Example 34, the method of any one or any combination of Examples 22-33 can optionally be configured such that advancing the guidewire in the retrograde direction includes advancing the guidewire until a free end of the guidewire is located outside the blood vessel.

In Example 35, the method of Example 34 can optionally be configured such that advancing the guidewire until the free end is located outside the blood vessel includes capturing the guidewire for externalization and exchange or subsequent use.

In Example 36, the assembly or method of any one or any combination of Examples 1-35 can optionally be configured such that all features, components, operations or other options are available to use or select from.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms, certain definitions shall be applied, unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" or "distally" refer to a position that is distant from, or in a direction away from, the treating clinician. "Proximal" and "proximally" refer to a position that is near, or in a direction toward, the treating clinician. The terms "antegrade" and "retrograde" are used to refer to directions relative to normal blood flow within a vessel. "Antegrade" refers to a direction that is the same as normal blood flow within the vessel. "Retrograde" refers to a direction that is opposite normal blood flow within the vessel.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   introducing a guide catheter into a blood vessel at a first entry site location;
   advancing the guide catheter in an antegrade direction toward an upstream, proximal end of an occlusion;
   introducing a capture catheter having a rapid exchange configuration into a proximal end portion of the guide catheter, the capture catheter including a longitudinal member having its distal end eccentrically coupled with a proximal end of an expandable member;
   advancing the capture catheter to a distal end portion of the guide catheter;
   deploying and expanding at least a portion of the expandable member of the capture catheter on the upstream, proximal end of the occlusion, including applying an advancing force, in a longitudinal direction and relative to the guide catheter, to a proximal end of the longitudinal member such that the expandable member is thereby advanced, in the longitudinal direction and relative to the guide catheter, to a position beyond the distal end portion of the guide catheter; and
   advancing a guidewire, introduced into the blood vessel at a second entry site location different than the first entry site location, in a retrograde direction, including advancing the guidewire toward and through a downstream, distal end of the occlusion and subsequently into and through the deployed expandable member on the upstream, proximal end of the occlusion.

2. The method of claim 1, wherein introducing the capture catheter into the proximal end portion of the guide catheter includes introducing an assembly including the capture catheter and a surrounding constraining catheter into the proximal end portion of the guide catheter.

3. The method of claim 2, further comprising withdrawing the capture catheter from the guide catheter, leaving the constraining catheter in place, and advancing a distal end portion of a tubular member of the constraining catheter beyond the distal end portion of the guide catheter.

4. The method of claim 1, wherein deploying and expanding at least the portion of the expandable member on the upstream, proximal end of the occlusion includes deploying and expanding at least a portion of a funnel member of the capture catheter.

5. The method of claim 4, wherein deploying and expanding at least the portion of the funnel member of the capture catheter includes allowing the portion of the funnel member to expand and bear against a luminal wall of the blood vessel adjacent to, but not beyond, the upstream, proximal end of the occlusion.

6. The method of claim 4, wherein advancing the capture catheter to the distal end portion of the guide catheter includes allowing blood flow through one or more perforations in each of a sidewall of the guide catheter and the funnel member of the capture catheter.

7. The method of claim 4, wherein the funnel member includes a decreasing inner diameter starting at its distal end and moving proximally.

8. The method of claim 1, wherein advancing the guidewire in the retrograde direction includes advancing the guidewire until a distal end portion of the guidewire is located outside the blood vessel.

9. The method of claim 8, wherein advancing the guidewire until the distal end portion is located outside the blood vessel includes capturing the guidewire for externalization and exchange or subsequent use.

10. The method of claim 9, further comprising:
introducing a treatment device over the distal end portion of the guidewire and into the proximal end portion of the guide catheter; and,
using the guidewire as a rail, advancing the treatment device in the antegrade direction to the occlusion for treatment thereof.

11. The method of claim 1, wherein deploying and expanding at least the portion of the expandable member on the upstream, proximal end of the occlusion includes inflating a balloon on the upstream, proximal end of the occlusion.

12. The method of claim 1, wherein advancing the guidewire in the retrograde direction includes receiving a distal end of the guidewire within a passage of the expandable member.

13. The method of claim 1, wherein advancing the guidewire in the retrograde direction includes introducing a support catheter over a proximal end portion of the guidewire at the second entry site and using the support catheter to provide column support to the guidewire.

14. The method of claim 1, wherein advancing the guidewire in the retrograde direction includes manipulating a distal end of the guidewire through the occlusion and creating a continuous channel between the occlusion's downstream, distal end and its upstream, proximal end.

15. The method of claim 1, wherein advancement of the guidewire in the retrograde direction toward and through the downstream, distal end of the occlusion occurs after deployment of the expandable member on the upstream, proximal end of the occlusion.

* * * * *